(12) United States Patent
Nakamura et al.

(10) Patent No.: US 12,020,499 B2
(45) Date of Patent: Jun. 25, 2024

(54) BIOLOGICAL INFORMATION ACQUISITION DEVICE, BIOLOGICAL AUTHENTICATION DEVICE, AND BIOLOGICAL INFORMATION ACQUISITION METHOD

(71) Applicant: PANASONIC INTELLECTUAL PROPERTY MANAGEMENT CO., LTD., Osaka (JP)

(72) Inventors: Hideyuki Nakamura, Fukuoka (JP); Risa Komatsu, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 18/034,269

(22) PCT Filed: Oct. 29, 2021

(86) PCT No.: PCT/JP2021/040176
§ 371 (c)(1),
(2) Date: Apr. 27, 2023

(87) PCT Pub. No.: WO2022/092305
PCT Pub. Date: May 5, 2022

(65) Prior Publication Data
US 2023/0394868 A1  Dec. 7, 2023

(30) Foreign Application Priority Data
Oct. 30, 2020  (JP) .................. 2020-182605

(51) Int. Cl.
*G06F 3/033*   (2013.01)
*G06V 40/10*   (2022.01)
(Continued)

(52) U.S. Cl.
CPC .......... *G06V 40/1312* (2022.01); *G06V 40/11* (2022.01); *G06V 40/50* (2022.01)

(58) Field of Classification Search
CPC .... G06V 40/1312; G06V 40/11; G06V 40/50; G06V 30/142; G06F 3/017; A61B 5/0531; H04N 13/204; H04N 21/4223
(Continued)

(56) References Cited

U.S. PATENT DOCUMENTS

2005/0286743 A1* 12/2005 Kurzweil ............. G06V 30/142
382/114
2009/0245585 A1  10/2009 Manabe et al.
(Continued)

FOREIGN PATENT DOCUMENTS

JP   2009-048387 A   3/2009
JP   2009-169705 A   7/2009
(Continued)

OTHER PUBLICATIONS

International Search Report (ISR) from International Searching Authority (Japan Patent Office) in International Pat. Appl. No. PCT/JP2021/040176, dated Dec. 21, 2021, together with an English language translation.
(Continued)

*Primary Examiner* — Abdul-Samad A Adediran
(74) *Attorney, Agent, or Firm* — Greenblum & Bernstein, P.L.C.

(57) ABSTRACT

This biological information acquisition device comprises: a first camera which captures a first hand image of a user, the hand being inserted into an imaging region; a second camera which captures a second hand image of the user used for biological authentication; and a processor which causes the second camera to capture the second hand image when a
(Continued)

stop of the user's hand is detected on the basis of the hand image captured by the first camera.

10 Claims, 11 Drawing Sheets

(51) Int. Cl.
    *G06V 40/13*     (2022.01)
    *G06V 40/50*     (2022.01)

(58) Field of Classification Search
    USPC ............ 345/158; 348/46; 382/114; 600/301; 715/743
    See application file for complete search history.

(56) References Cited

U.S. PATENT DOCUMENTS

| | | | | |
|---|---|---|---|---|
| 2012/0235903 | A1* | 9/2012 | Im | G06F 3/017 |
| | | | | 345/158 |
| 2014/0152773 | A1* | 6/2014 | Ohba | H04N 13/204 |
| | | | | 348/46 |
| 2014/0229845 | A1* | 8/2014 | Ivanich | H04N 21/4223 |
| | | | | 715/743 |
| 2023/0210382 | A1* | 7/2023 | Wang | A61B 5/0531 |
| | | | | 600/301 |

FOREIGN PATENT DOCUMENTS

| | | | |
|---|---|---|---|
| JP | 2009-240523 | A | 10/2009 |
| JP | 2010-086263 | A | 4/2010 |
| JP | 2010-287247 | A | 12/2010 |
| JP | 2011-013710 | A | 1/2011 |

OTHER PUBLICATIONS

Written Opinion (WO) from International Searching Authority (Japan Patent Office) in International Pat. Appl. No. PCT/JP2021/040176, dated Dec. 21, 2021, together with an English language translation.

Extended European Search Report (EESR) from European Patent Office (EPO) in European Patent Appl. No. 21886422.1, dated Mar. 5, 2024.

Imura et al., "A Hand Gesture-Based Method for Biometric Authentication", Jun. 1, 2018 (Jun. 1, 2018), Jun. 1, 2018, pp. 554-566.

* cited by examiner

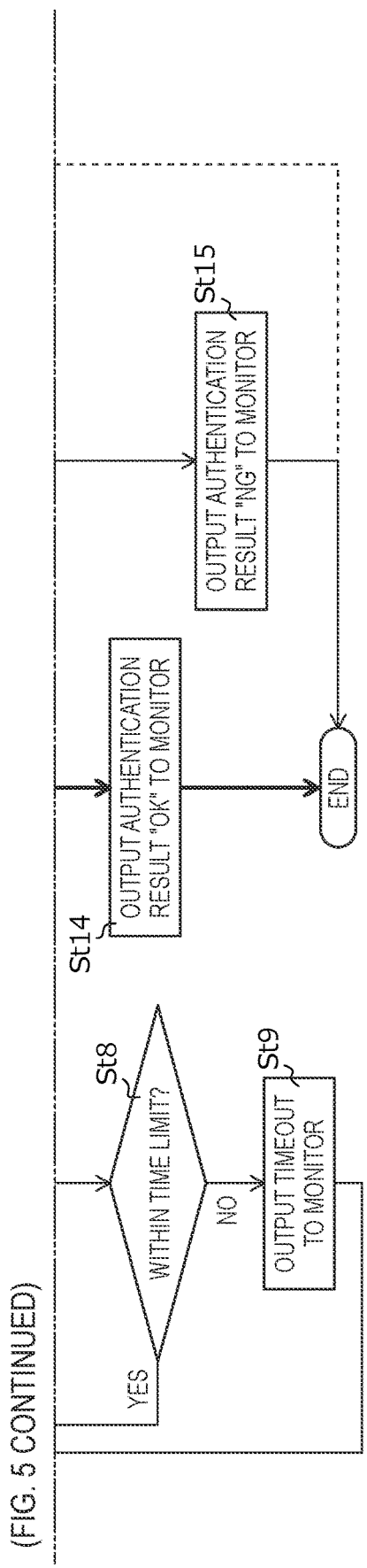

BIOLOGICAL INFORMATION ACQUISITION DEVICE, BIOLOGICAL AUTHENTICATION DEVICE, AND BIOLOGICAL INFORMATION ACQUISITION METHOD

TECHNICAL FIELD

The present disclosure relates to a biological information acquisition device, a biological authentication device, and a biological information acquisition method.

BACKGROUND ART

Patent Literature 1 discloses a blood vessel pattern extraction device including a finger placement unit which guides a finger to a predetermined position, a light source which irradiates the finger with light, an opening portion through which transmission light that is emitted to the finger and transmitted through the finger passes and which is formed in the finger placement unit, and an imaging unit which images the transmission light passing through the opening portion. The blood vessel pattern extraction device includes a tip end holding portion which holds a tip end side of the finger and a base holding portion which holds a base side of the finger. The transmission light transmitted through the finger passes through the opening portion disposed between the tip end holding portion and the base holding portion. The finger placed between the tip end holding portion and the base holding portion is not in contact with the opening portion. The light source is disposed obliquely upward with respect to the finger placement unit, and a gap opened above the finger placement unit is formed.

CITATION LIST

Patent Literature

Patent Literature 1: JP2010-287247A

SUMMARY OF INVENTION

Technical Problem

Here, a biological authentication device using a finger is mainly a contact type biological authentication device that fixes and authenticates a finger such that authentication accuracy does not decrease due to camera shake or the like. In addition, in recent years, there has been an increasing demand for a biological authentication device, in which an opportunity of contact via an unspecified large number of persons and objects is reduced, from a hygiene viewpoint such as a virus infection countermeasure. However, in the configuration of Patent Literature 1, although the tip end side (for example, the vicinity of a first joint to a second joint) of the finger is not in contact with a glass surface of the opening portion, in order not to lower the authentication accuracy, the base side of the finger is brought into contact with and fixed to the base holding portion, and therefore, there is room for improvement in achieving acquisition of biological information by a non-contact type biological authentication device.

The present disclosure has been made in view of the above-described conventional circumstances, and an object of the present disclosure is to provide a biological information acquisition device, a biological authentication device, and a biological information acquisition method capable of stably acquiring a hand image used for biological authentication even in a non-contact state.

Solution to Problem

The present disclosure provides a biological information acquisition device including a first camera configured to capture a first hand image of a user inserted into an imaging region, a second camera configured to capture a second hand image of the user used for biological authentication, and a processor configured to cause the second camera to capture the second hand image used for the biological authentication when a stationary state of a hand of the user is detected based on the first hand image captured by the first camera.

In addition, the present disclosure provides a biological authentication device including a first camera configured to image a hand of a user inserted into an imaging region, a second camera configured to image the hand of the user, a processor configured to cause the second camera to image the hand when a stationary state of the hand is detected based on a first hand image of the user captured by the first camera, and an output unit configured to acquire biological information of the user based on a second hand image of the user captured by the second camera, and output a collation result obtained by collating the acquired biological information with biological information of a plurality of users registered in advance.

In addition, the present disclosure provides a biological information acquisition method of a biological information acquisition device that images a hand of a user using two cameras. The biological information acquisition method includes imaging, by a first camera, the hand of the user inserted into an imaging region, and imaging the hand of the user by a second camera when a stationary state of the hand is detected based on a captured hand image of the user.

Advantageous Effects of Invention

According to the present disclosure, it is possible to stably acquire a hand image used for biological authentication even in a non-contact state.

5 and an operation procedure example of the biological authentication system according to each embodiment.

Figure 10:
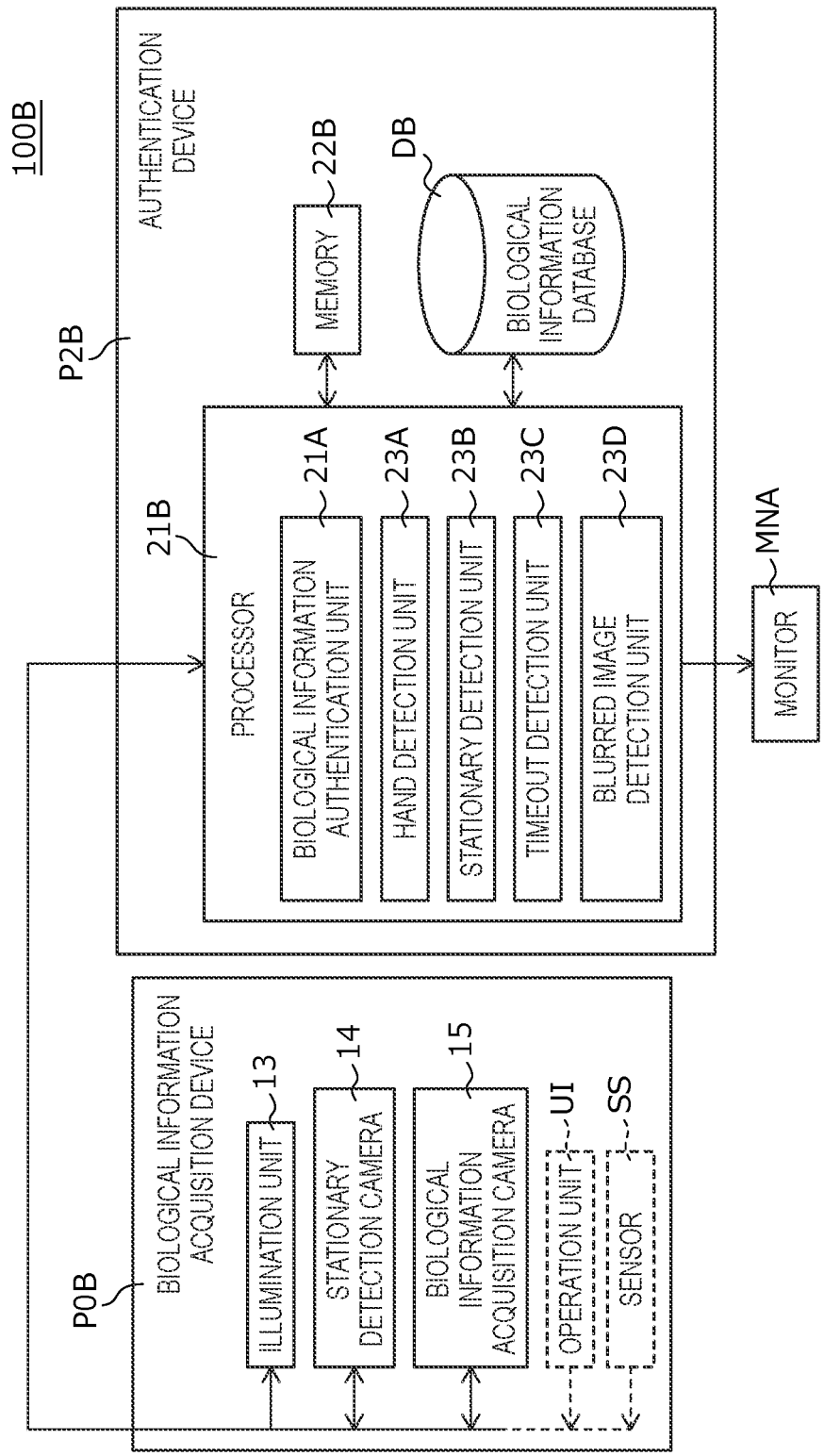

FIG. 10 is a diagram illustrating an internal configuration example of a biological information acquisition device and an authentication device according to a third embodiment.

DESCRIPTION OF EMBODIMENTS

Hereinafter, embodiments in which a configuration and an operation of a biological information acquisition device, a biological authentication device, and a biological information acquisition method according to the present disclosure are specifically disclosed will be described in detail with reference to the drawings as appropriate. However, unnecessarily detailed description may be omitted. For example, detailed description of well-known matters and redundant description of substantially the same configuration may be omitted. This is to avoid unnecessary redundancy of the following description and to facilitate understanding of those skilled in the art. The accompanying drawings and the following description are provided for those skilled in the art to fully understand the present disclosure, and are not intended to limit the subject matters described in the claims.

Here, the terms used in the following description are merely examples, and are not intended to limit the scope of the present disclosure. For example, the term "biological information" includes a captured image (authentication hand image) including a part of a hand of a user used for extraction of biological information.

First Embodiment

Figure 1:
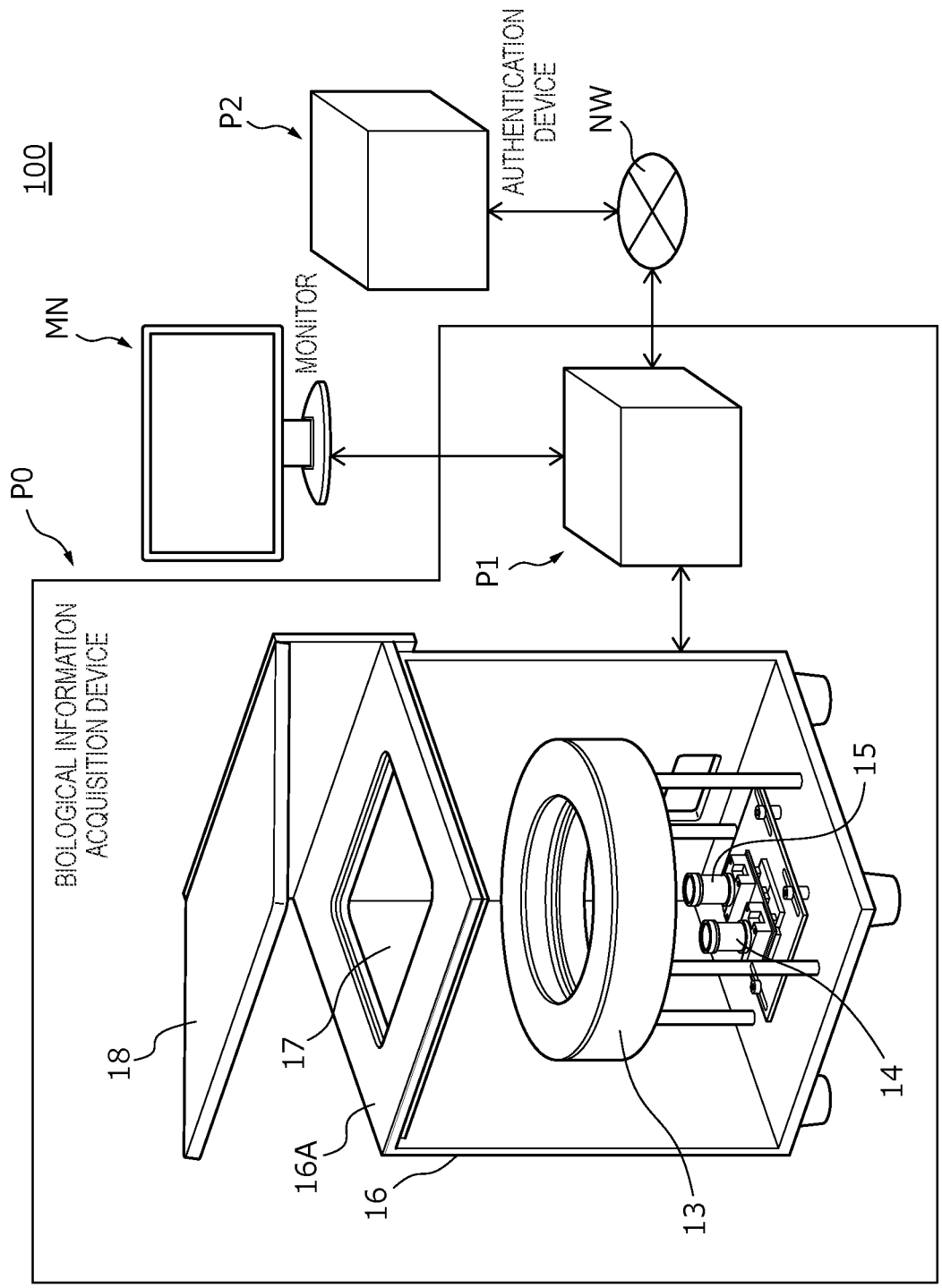
FIG. 1 is a diagram illustrating an overall configuration example of a biological authentication system according to a first embodiment.
Figure 2:
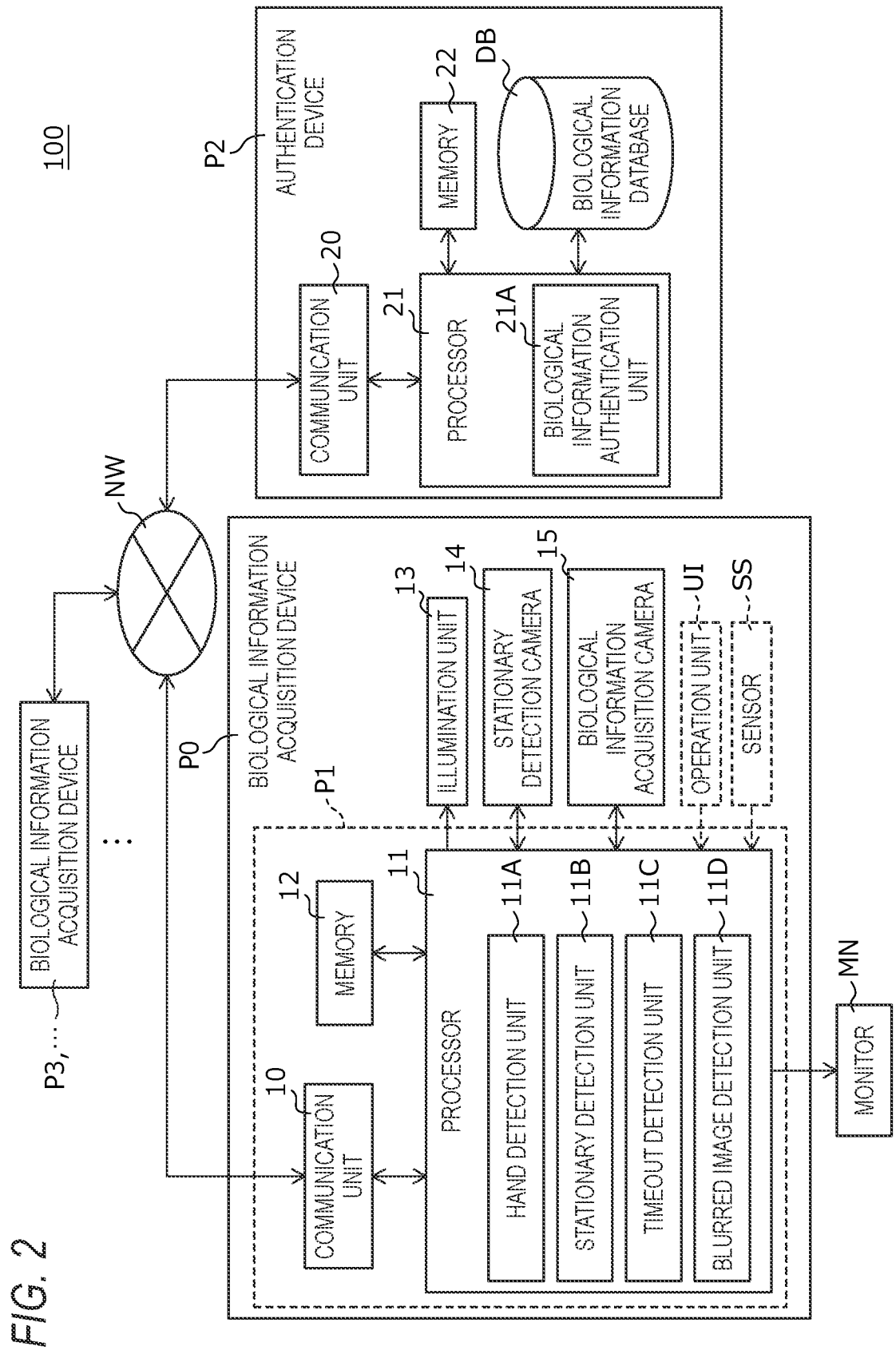
FIG. 2 is a diagram illustrating an internal configuration example of a biological information acquisition device and an authentication device according to the first embodiment.

An overall configuration example of a biological authentication system 100 according to a first embodiment will be described with reference to FIGS. 1 and 2. FIG. 1 is a diagram illustrating the overall configuration example of the biological authentication system 100 according to the first embodiment. FIG. 2 is a diagram illustrating an internal configuration example of a biological information acquisition device P0 and an authentication device P2 according to the first embodiment.

The biological authentication system 100 according to the first embodiment extracts and acquires biological information of a user based on a captured image (hereinafter referred to as an "authentication hand image") obtained by capturing a part of a hand of the user. In addition, the biological authentication system 100 collates the acquired biological information of the user with biological information of a plurality of users registered in advance, executes user authentication, and outputs an authentication result. The biological information referred to here may be biological information based on a fingerprint of the user or biological information based on a vein of a finger of the user.

The biological authentication system 100 according to the first embodiment includes the biological information acquisition device P0, the authentication device P2, a network NW, and a monitor MN. The biological information acquisition device P0 and the authentication device P2 are connected to each other via the network NW in a manner of wireless communication or wired communication, and transmit and receive data. The wireless communication referred to here is, for example, communication via a wireless local area network (LAN) such as Wi-Fi (registered trademark).

The biological information acquisition device P0 is connected to the authentication device P2 via the network NW such that data communication can be performed between the biological information acquisition device P0 and the authentication device P2. When it is detected by a stationary detection camera 14 that the hand of the user is stationary based on a captured image (hereinafter referred to as a "detection hand image") obtained by imaging the hand of the user inserted into an imaging region (specifically, a space between a glass surface 17 and a cover guide 18 and above the glass surface 17), the biological information acquisition device P0 images a part of the hand of the user by a biological information acquisition camera 15. The biological information acquisition device P0 acquires an authentication image, generates a finger image obtained by partially segmenting a partial region of the finger from the authentication hand image, and transmits the finger image as the acquired biological information of the user to the authentication device P2. The biological information acquisition device P0 transmits, to the authentication device P2, biological information of the user extracted based on the finger image. The biological information acquisition device P0 outputs, to the monitor MN, the authentication result executed by the authentication device P2 using the finger image or the biological information of the user.

The biological information acquisition device P0 includes a control device P1, an illumination unit 13, the stationary detection camera 14, the biological information acquisition camera 15, a housing 16, the glass surface 17, and the cover guide 18. Although the biological information acquisition device P0 shown in FIG. 1 illustrates an example in which the control device P1 is disposed outside the housing 16, the control device P1 may be incorporated in the housing 16. In addition, an operation unit UI and a sensor SS are not necessary components and may be omitted.

The control device P1 is implemented with, for example, a personal computer (PC), and executes various types of control processing in the biological information acquisition device P0. The control device P1 implements various functions of a communication unit 10, a processor 11, and a memory 12.

The communication unit 10 is connected to a communication unit 20 in the authentication device P2 via the network NW in a manner of wireless communication or wired communication, and executes transmission and reception of data. The communication unit 10 transmits the finger image of the user or the biological information of the user, which are output from the processor 11, to the authentication device P2, and outputs the authentication result transmitted from the authentication device P2 to the processor 11. The finger image of the user or the biological information of the user, which are transmitted to the authentication device P2, may be subjected to encryption processing.

The processor 11 is implemented using, for example, a central processing unit (CPU) or a field programmable gate array (FPGA), and performs various types of processing and control in cooperation with the memory 12. Specifically, the processor 11 refers to a program and data stored in the memory 12, and executes the program to implement the functions of the units for acquiring the hand image of the user or the biological information of the user. The units referred to here include a hand detection unit 11A, a stationary detection unit 11B, a timeout detection unit 11C, and a blurred image detection unit 11D.

The hand detection unit 11A determines (detects), based on the detection hand image captured by the stationary detection camera 14, whether the hand of the user is inserted into the imaging region. The hand detection unit 11A executes insertion detection processing of the hand for each frame. Here, the insertion detection processing of the hand executed by the hand detection unit 11A will be described in detail with reference to FIG. 3.

The stationary detection unit 11B determines (detects) whether the hand of the user is stationary based on the detection hand image captured by the stationary detection camera 14. The stationary detection unit 11B executes stationary detection processing of the hand for each frame. The stationary detection processing of the hand executed by the stationary detection unit 11B will be described in detail with reference to FIG. 4.

The timeout detection unit 11C determines whether a stationary state of the hand of the user is detected within a predetermined time limit set in advance from a timing at which the insertion of the hand of the user into the imaging region is detected by the hand detection unit 11A. When the stationary state of the hand of the user is not detected within the predetermined time limit, the timeout detection unit 11C generates a timeout notification screen MN1 (see FIG. 6) notifying that a timeout has occurred, and outputs the timeout notification screen MN1 to the monitor MN.

The blurred image detection unit 11D determines whether the authentication hand image is blurred based on the authentication hand image captured by the biological information acquisition camera 15. Here, the blur referred to here indicates a motion blur that occurs when a subject moves, and indicates, for example, a trajectory (an afterimage) of the hand remaining in the captured image by moving the hand as the subject at a high speed. When it is determined that the authentication hand image is not blurred, the blurred image detection unit 11D generates a finger image obtained by segmenting a range, in which a part of the finger of the user is shown, from the acquired authentication hand image, performs the encryption processing on the finger image, and transmits the finger image to the authentication device P2. The blurred image detection unit 11D may extract the biological information of the user by using the generated finger image, perform the encryption processing on the extracted biological information of the user, and transmit the biological information to the authentication device P2. The extraction processing of the biological information of the user using the finger image will be described later.

Here, a method of generating the finger image will be described. The blurred image detection unit 11D detects the finger of the user based on the authentication hand image, and generates a finger image obtained by segmenting a region including a part of at least one detected finger of the user. The method of generating the finger image is not limited thereto, and other known techniques may be used.

The memory 12 includes, for example, a random access memory (RAM) as a work memory used when each processing of the processor 11 is executed, and a read only memory (ROM) storing a program and data defining an operation of the processor 11. The RAM temporarily stores data or information generated or acquired by the processor 11. The program that defines the operation of the processor 11 is written in the ROM.

The illumination unit 13 is housed inside the housing 16 of the biological information acquisition device P0, and is disposed between the stationary detection camera 14 and the glass surface 17 and between the biological information acquisition camera 15 and the glass surface 17. The illumination unit 13 includes one or more illuminations such as a light emitting diode (LED), a fluorescent lamp, an incandescent lamp, and an infrared (IR) illumination, and illuminates the hand of the user positioned in the imaging region. The illumination unit 13 executes control to turn on or off the illumination based on a control command output from the processor 11. In FIG. 1, the illumination unit 13 formed in an annular shape is illustrated as an example, and the present disclosure is not limited thereto. For example, the illumination unit 13 may be a point light source, or may be configured such that a plurality of illuminations are disposed to have a polygonal shape or a substantially annular shape.

The stationary detection camera 14 as an example of a first camera includes at least an image sensor (not illustrated) and a lens (not illustrated). The image sensor is, for example, a solid-state imaging device such as a charge-coupled device (CCD) or a complementary metal oxide semiconductor (CMOS), and converts an optical image formed on an imaging surface into an electrical signal. The stationary detection camera 14 has a frame rate higher than that of the biological information acquisition camera 15 and a resolution lower than that of the biological information acquisition camera 15. The stationary detection camera 14 used in the biological information acquisition device P0 is, for example, a camera having a frame rate of 60 fps and a resolution of 640×480.

The biological information acquisition camera 15 as an example of a second camera includes at least an image sensor (not illustrated) and a lens (not illustrated). The image sensor is, for example, a solid-state imaging device such as a CCD or a CMOS, and converts an optical image formed on an imaging surface into an electrical signal. The biological information acquisition camera 15 has a frame rate lower than that of the stationary detection camera 14 and a resolution higher than that of the stationary detection camera 14. The biological information acquisition camera 15 used in the biological information acquisition device P0 is, for example, a camera having a frame rate of 1 fps and a resolution of 3280×2464.

The housing 16 is made of metal or resin, and houses the illumination unit 13, the stationary detection camera 14, and the biological information acquisition camera 15. The housing 16 may house the control device P1. The stationary detection camera 14 and the biological information acquisition camera 15 are disposed adjacent to each other, and image a part of the hand of the user illuminated by the illumination unit 13.

The glass surface 17 is provided on a housing upper surface 16A of the housing 16, and enables the illumination unit 13 to illuminate the hand of the user and enables the stationary detection camera 14 and the biological information acquisition camera 15 to image the hand of the user.

The cover guide 18 is formed in a substantially L-shape with a metal or a resin as a material. One end of the substantially L-shaped cover guide 18 is fixed to any one side of the rectangular housing upper surface 16A. In addition, the other end of the substantially L-shaped cover guide 18 covers the housing upper surface 16A and the glass surface 17.

The other end side of the substantially L-shaped cover guide 18 is formed such that a distance (that is, a height) between the housing upper surface 16A and a lower surface of the cover guide 18 (that is, a surface on a side facing the glass surface 17) increases (is higher) from the side, among the four sides of the housing upper surface 16A, to which the one end of the cover guide 18 is fixed toward the opposite side. That is, the cover guide 18 is provided such that the distance (that is, the height) between the housing upper surface 16A and the cover guide 18 increases on a side where the user is positioned (a side of the side facing the one side to which the one end of the substantially L-shape is fixed). Therefore, in the biological information acquisition device P0, the distance (height) between the housing upper surface 16A and the cover guide 18 is the highest toward the side where the user is positioned, and thus the user can easily insert the hand into the imaging region.

The operation unit UI can receive an operation by an administrator (for example, a specific person such as a security guard and an administrator of a facility and a building in which the biological information acquisition device P0 is disposed, or an employee of a store in which the biological information acquisition device P0 is disposed), and is implemented with, for example, a button, a mouse, a keyboard, and a touch panel. The operation unit UI outputs the received operation of the administrator to the processor 11.

Specifically, the sensor SS is a reflection type time of flight (TOF) sensor, an infrared sensor, a transmission type laser sensor, a light receiving sensor, or the like. One or more sensors SS are provided around the glass surface 17 on the housing upper surface 16A, and detect the hand of the user inserted into the imaging region. When the hand of the user is detected, the sensor SS generates a detection signal and outputs the detection signal to the processor 11.

The authentication device P2 extracts the biological information of the user using a finger image of the user transmitted from each of a plurality of biological information acquisition devices P0, P3, . . . via the network NW. As the extraction of the biological information, a known technique (for example, the technique disclosed in JP2018-124999A) may be used. The authentication device P2 collates the extracted biological information with the biological information of the plurality of users registered in advance by an administrator or the like of the biological authentication system 100 or the biological information acquisition devices. The authentication device P2 determines whether the extracted biological information matches any of the registered biological information of the plurality of users, executes user authentication processing, and transmits determination results to the biological information acquisition devices. The authentication device P2 includes the communication unit 20, a processor 21, a memory 22, and a biological information database DB.

The communication unit 20 is connected to a communication unit in each of the plurality of biological information acquisition devices P0, P3, . . . via the network NW in a manner of wireless communication or wired communication, and executes transmission and reception of data. The communication unit 20 outputs finger images of the user transmitted from the biological information acquisition devices to the processor 21, and transmits authentication results output from the processor 21 to the biological information acquisition devices. The authentication results transmitted to the biological information acquisition devices may be subjected to the encryption processing. In addition, the finger images or the biological information of the user transmitted from the plurality of biological information acquisition devices P0, . . . to the authentication device P2 may be subjected to the encryption processing by the biological information acquisition devices P0, P3, . . . . The plurality of biological information acquisition devices P0, P3, . . . execute the encryption processing on the finger images or the biological information of the user to be transmitted, so that it is possible to more accurately prevent the finger images or the biological information of the user from leaking in transmission processing to the authentication device P2.

The processor 21 is implemented using, for example, a central processing unit (CPU) or a field programmable gate array (FPGA), and performs various types of processing and control in cooperation with the memory 22. Specifically, the processor 21 refers to a program and data stored in the memory 22, and executes the program to implement a function of a biological information authentication unit 21A for executing user authentication.

The biological information authentication unit 21A extracts the biological information of the user based on the finger image of the user. The biological information authentication unit 21A collates the extracted biological information of the user with biological information of the plurality of users stored (registered) in the biological information database DB. The authentication device P2 generates an authentication result indicating whether the extracted biological information of the user matches any of the registered biological information of the plurality of users, outputs the authentication result to the communication unit 20, and causes the biological information acquisition devices to transmit the authentication result.

The memory 22 includes, for example, a RAM as a work memory used when each processing of the processor 21 is executed, and a ROM that stores a program and data defining an operation of the processor 21. The RAM temporarily stores data or information generated or acquired by the processor 21. The program that defines the operation of the processor 21 is written in the ROM.

The biological information database DB stores (registers) the biological information for each user and information (for example, a name, an identification number, and a face picture) related to the plurality of users registered in advance by the administrator or the like of the biological authentication system 100 or the biological information acquisition devices in association with each other.

The one or more biological information acquisition devices P3, . . . are connected to the authentication device P2 via the network NW in a manner of data communication. The biological information acquisition devices P3 . . . acquire finger images including the biological information of the user, perform the encryption processing on the acquired finger images, and transmit the encrypted finger images to the authentication device P2. In addition, the biological information acquisition devices P3, . . . output, to the monitor MN, the authentication result generated by the authentication device P2 for the transmitted finger images or biological information of the user. Since configurations of the biological information acquisition devices P3, . . . are the same as that of the biological information acquisition device P0, the description thereof is omitted.

The network NW connects the biological information acquisition devices P0, P3, . . . and the authentication device P2 in a manner of data communication.

Figure 3:
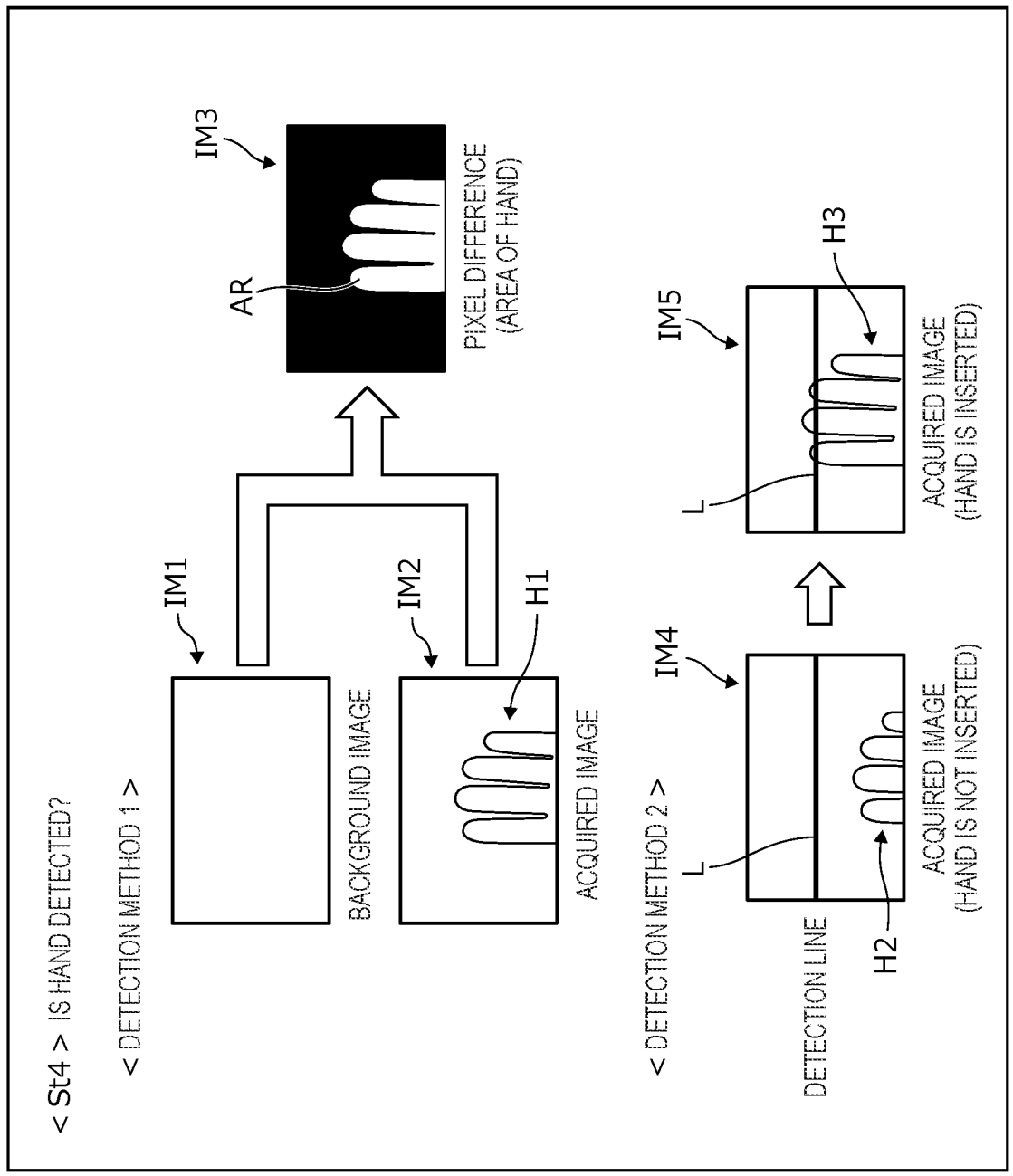
FIG. 3 is a diagram illustrating an example of insertion detection of a hand.

Next, an example of insertion detection of the hand executed by the hand detection unit 11A will be described with reference to FIG. 3. FIG. 3 is a diagram illustrating the example of the insertion detection of the hand. The insertion detection processing of the hand illustrated in FIG. 3 corresponds to processing of step St4 in a flowchart illustrating an example of a processing procedure of the biological authentication system 100 illustrated in FIG. 5.

The hand detection unit 11A in a detection method 1 compares a background image IM1 captured in advance with a detection hand image IM2 captured by the stationary detection camera 14. Here, the background image IM1 is a captured image captured by the stationary detection camera 14 in advance, for example, when the biological information acquisition device P0 is disposed, and is a captured image obtained by imaging a surface of the cover guide 18 facing the glass surface 17. The hand detection unit 11A calculates a pixel difference between the background image IM1 and the detection hand image IM2. That is, the pixel difference calculated here indicates, for example, as illustrated in a difference image IM3, an area AR of a hand H1 of the user shown in the detection hand image IM2. The hand detection unit 11A determines whether the calculated pixel difference (that is, the area AR of the hand H1 of the user) is equal to or greater than a predetermined value (for example, 30% or more with respect to a total area (the number of pixels) of an angle of view of the stationary detection camera 14), and detects the insertion of the hand of the user when it is determined that the pixel difference (that is, the area AR of the hand H1 of the user) is equal to or greater than the predetermined value.

In addition, the hand detection unit 11A in a detection method 2 detects the hand of the user from the acquired detection hand image, and determines whether the hand of the user exceeds a detection line L for detecting the hand with respect to the angle of view of the stationary detection camera 14 set in advance by the detected hand of the user (that is, whether the hand of the user is positioned above the detection line L).

For example, in an example of a detection hand image IM4 illustrated in FIG. 3, after a hand H2 of the user is detected from the acquired detection hand image IM4, the hand detection unit 11A determines whether the detected hand H2 exceeds the detection line L. The hand detection unit 11A determines, as a result of the determination, that the detected hand H2 does not exceed the detection line L, and outputs, as a detection result, a notification indicating that the insertion of the hand cannot be detected (that is, the hand is not inserted). On the other hand, in an example of a detection hand image IM5 illustrated in FIG. 4, after a hand H3 of the user is detected from the acquired detection hand image IM5, the stationary detection unit 1/ B determines whether the detected hand H3 exceeds the detection line L. The hand detection unit 11A determines, as a result of the determination, that the detected hand H3 exceeds the detection line L, and outputs, as a detection result, a notification indicating that the insertion of the hand is detected (that is, the hand is inserted).

The insertion detection of the hand executed by the hand detection unit 11A may use at least one of the detection method 1 and the detection method 2, or use both the detection method 1 and the detection method 2.

Figure 4:
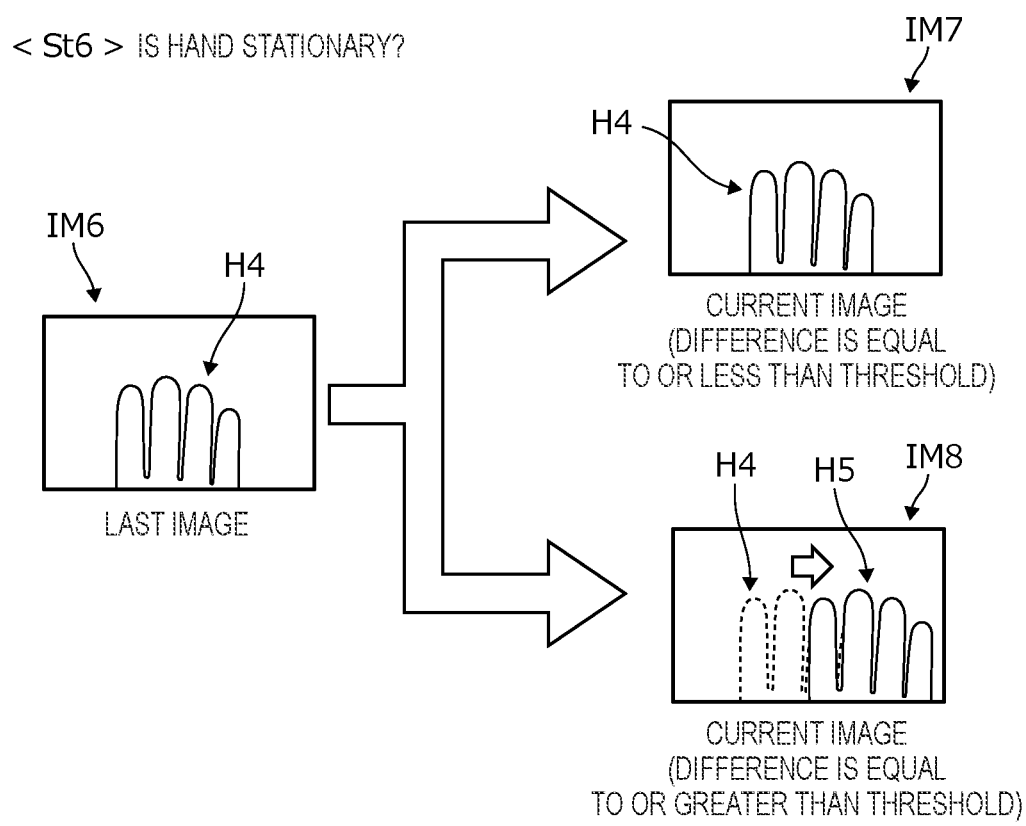
FIG. 4 is a diagram illustrating an example of stationary detection of the hand.

Next, an example of stationary detection of the hand executed by the stationary detection unit 11B will be described with reference to FIG. 4. FIG. 4 is a diagram illustrating the example of the stationary detection of the hand. The stationary detection processing of the hand illustrated in FIG. 4 corresponds to processing of step St6 in the flowchart illustrating the example of the processing procedure of the biological authentication system 100 illustrated in FIG. 5.

The stationary detection unit 11B calculates a difference for each pixel between the hand H1 (see FIG. 3) shown in the detection hand image IM2 in which the insertion of the hand of the user is detected or the hand H3 (see FIG. 3) shown in the detection hand image IM5 and a hand H4 shown in a latest detection hand image IM6 captured next to the detection hand image IM2 or the detection hand image IM5. For example, as in a difference image IM7 illustrated in FIG. 4, when a difference (that is, a movement amount) between positions of the hand H4 of the user shown in two detection hand images is sufficiently small, a calculated difference for each pixel between the two detection hand images is small. In addition, as in a difference image IM8 illustrated in FIG. 4, when a difference between positions of the hands H4 and H5 of the user shown in two detection hand images is large, a calculated difference for each pixel between the two detection hand images is large. The stationary detection unit 11B determines whether the calculated difference for each pixel is equal to or less than a threshold set in advance. When the stationary detection unit 11B determines that the difference for each pixel is equal to or less than the threshold, the stationary detection unit 11B outputs, as a detection result, a notification indicating that the hand of the user is detected to be in a stationary state. On the other hand, when the stationary detection unit 11B determines that the difference for each pixel is not equal to or less than the threshold, the stationary detection unit 11B outputs, as a detection result, a notification indicating that the hand of the user is not stationary.

The detection hand image used for the stationary detection is not limited to the hand H1 (see FIG. 3) shown in the detection hand image IM2 in which the insertion of the hand of the user is detected or the hand H3 (see FIG. 3) shown in the detection hand image IM5. The stationary detection unit 11B may execute the stationary detection processing of the hand of the user using two detection hand images continuously captured after the insertion of the hand of the user is detected. Specifically, the stationary detection unit 11B may execute the stationary detection processing of the hand of the user using the two detection hand images captured after the insertion of the hand of the user is detected.

Figure 5:
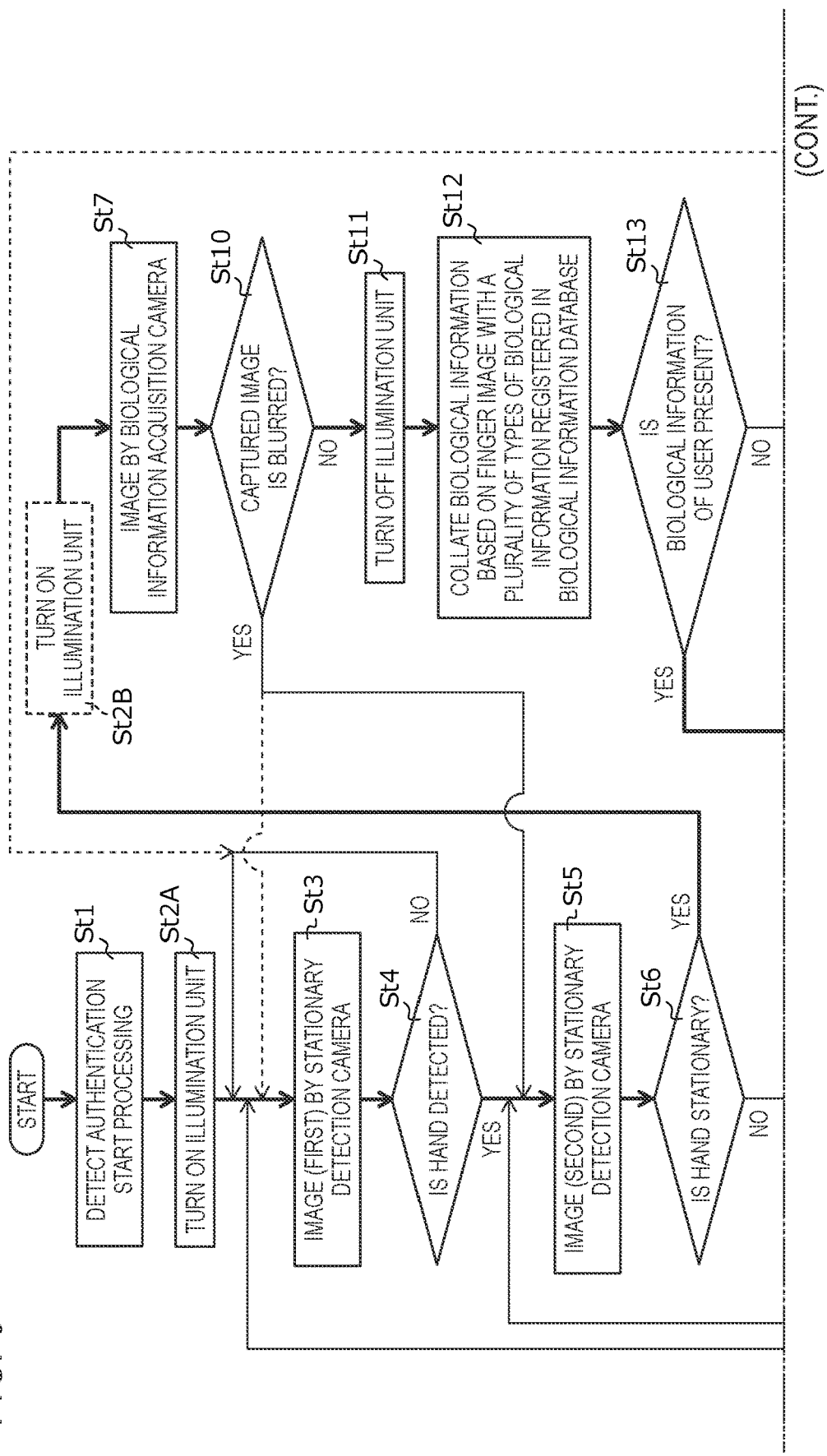
FIG. 5 is a flowchart illustrating an example of a processing procedure of the biological authentication system according to the first embodiment.

The processing procedure of the biological authentication system 100 according to the first embodiment will be described with reference to FIG. 5. FIG. 5 is a flowchart illustrating the example of the processing procedure of the biological authentication system 100 according to the first embodiment.

When authentication start processing is detected (St1), the biological information acquisition device P0 turns on the illumination unit 13 (St2A). The authentication start processing referred to here is reception of an administrator operation by the operation unit UI, a power-on operation of the biological information acquisition device P0 by the administrator, detection of the hand of the user by the sensor SS, or the like. In addition, the biological information acquisition device P0 may turn on the illumination unit 13 before processing of step St7 to be described later.

After the illumination unit 13 is turned on, the biological information acquisition device P0 executes first imaging by the stationary detection camera 14 (St3), and determines whether the hand of the user is inserted into the imaging region based on the captured detection hand image of the user (St4). The insertion detection (determination) of the hand of the user is detected (determined) by the detection method 1 or the detection method 2, or both the detection method 1 and the detection method 2 illustrated in FIG. 3.

When it is determined in the processing of step St4 that the hand of the user is inserted into the imaging region (St4, YES), the biological information acquisition device P0 starts measuring an elapsed time until the stationary state of the hand of the user is detected, and executes second imaging by the stationary detection camera 14 (St5).

On the other hand, when it is determined in the processing of step St4 that the hand of the user is not inserted into the imaging region (St4, NO), the biological information acquisition device P0 returns to the processing of step St3, and captures a detection hand image used for the insertion detection of the hand again.

The biological information acquisition device P0 determines whether a motion of the hand of the user is stationary based on the detection hand image acquired by the first imaging of the stationary detection camera 14 (that is, the detection hand image used for the stationary detection of the hand of the user in the processing of step St4) and the detection hand image acquired by the second imaging of the stationary detection camera 14 in step St5 (St6). The stationary detection of the hand of the user is detected by a stationary detection method illustrated in FIG. 4. In addition, the detection hand image used in the stationary detection processing of the hand of the user may be two detection hand images continuously captured by the stationary detection camera 14 in the processing of step St5.

When it is determined in the processing of step St6 that the motion of the hand of the user is stationary (St6, YES), the biological information acquisition device P0 executes imaging of the hand of the user by the biological information acquisition camera 15 (St7).

On the other hand, when it is determined in the processing of step St6 that the motion of the hand of the user is not stationary (St6, YES), the biological information acquisition device P0 determines whether an elapsed time, from a timing at which the insertion of the hand of the user is detected to a timing at which it is determined that the motion of the hand of the user is not stationary, within a predetermined time limit set in advance (that is, whether the stationary detection processing of the hand has timed out) (St8). Since the illumination unit 13 only needs to be turned on at the time of capturing the authentication hand image by the biological information acquisition camera 15, when it is determined that the motion of the hand of the user is stationary (St6, YES), the biological information acquisition device P0 may turn on the illumination unit 13 (St2B).

When it is determined in the processing of step St8 that the elapsed time is within the predetermined time limit set in advance (that is, the stationary detection processing of the hand has not timed out) (St8, YES), the biological information acquisition device P0 returns to the processing of step St5, continues the measurement of the elapsed time, and executes the second imaging processing by the stationary detection camera 14.

On the other hand, when it is determined in the processing of step St8 that the elapsed time is not within the predetermined time limit set in advance (that is, the stationary detection processing of the hand has timed out) (St8, NO), the biological information acquisition device P0 generates the timeout notification screen MN1 (see FIG. 6), outputs the timeout notification screen MN1 to the monitor MN (St9), and causes the monitor MN to display the timeout notification screen MN1.

The biological information acquisition device P0 determines whether the authentication hand image captured by the biological information acquisition camera 15 is blurred (St10).

When it is determined in the processing of step St10 that the hand of the user shown in the authentication hand image is blurred (St10, YES), the biological information acquisition device P0 returns to the processing of step St5 and executes the second imaging processing by the stationary detection camera 14. Measurement processing of the elapsed time may be continued until the processing of step St10 is completed, or may be reset at a timing when it is determined in the processing of step St6 that the motion of the hand of the user is stationary. In addition, when it is determined that the hand of the user shown in the authentication hand image is blurred (St10, YES), the biological information acquisition device P0 may return to the processing of step St3 and execute the first imaging processing by the stationary detection camera 14.

On the other hand, when it is determined in the processing of step St10 that the hand of the user shown in the authentication hand image is not blurred (St10, NO), the biological information acquisition device P0 turns off the illumination unit 13 (St11). The biological information acquisition device P0 generates a finger image obtained by segmenting a region showing a part of at least one finger of the user from the authentication hand image captured by the biological information acquisition camera 15, performs the encryption processing on the finger image, and transmits the finger image to the authentication device P2. The biological information acquisition device P0 may extract the biological information of the user based on the generated finger image, perform the encryption processing on the extracted biological information of the user, and transmit the biological information to the authentication device P2.

The authentication device P2 extracts the biological information of the user based on the finger image of the user transmitted from the biological information acquisition device P0. The authentication device P2 collates the extracted biological information of the user with the biological information of the plurality of users stored (registered) in the biological information database DB (St12). The authentication device P2 determines whether the extracted biological information of the user is present in the biological information of the plurality of users stored (registered) in the biological information database DB (St13).

When it is determined in the processing of step St13 that the extracted biological information of the user is present in the biological information of the plurality of users stored (registered) in the biological information database DB (St13, YES), the authentication device P2 generates an authentication result notification screen MN2 (see FIG. 7) indicating that the authentication result of the user authentication is "OK", and transmits the authentication result notification screen MN2 to the biological information acquisition device P0. The biological information acquisition device P0 outputs, to the monitor MN, the authentication result notification screen MN2 transmitted from the authentication device P2 (St14), and causes the monitor MN to display the authentication result notification screen MN2.

On the other hand, when it is determined in the processing of step St13 that the extracted biological information of the user is not present in the biological information of the plurality of users stored (registered) in the biological information database DB (St13, NO), the authentication device P2 generates an authentication result notification screen MN3 (see FIG. 7) indicating that the authentication result of the user authentication is "NG", and transmits the authentication result notification screen MN3 to the biological information acquisition device P0. The biological information acquisition device P0 outputs, to the monitor MN, the authentication result notification screen MN2 transmitted from the authentication device P2 (St15), and causes the monitor MN to display the authentication result notification screen MN2. When it is determined in the processing of step St13 that the extracted biological information of the user is not present in the biological information of the plurality of users stored (registered) in the biological information database DB (St13, NO), the authentication device P2 may return to the processing of step St3.

As described above, the biological authentication system 100 according to the first embodiment acquires the authentication hand image as the biological information and executes the user authentication. The biological authentication system 100 may return to the processing of step St2A or step St3 after the processing of step St14, and repeatedly acquire the authentication hand images as the biological information for the plurality of users and execute the user authentication. When the detection of the authentication start processing illustrated in step St1 is executed by the detection of the hand of the user by the sensor SS, the biological authentication system 100 may return to the processing of step St1 after the processing of step St14, and repeatedly acquire the authentication hand images as the biological information for the plurality of users and execute the user authentication.

In addition, the biological authentication system 100 may execute the detection of the authentication start processing illustrated in step St1 based on the insertion detection of the hand of the user. In such a case, an operation procedure example of the biological authentication system 100 illustrated in FIG. 5 starts from the processing of step St3, and when the insertion of the hand of the user is detected in the processing of step St4, it is determined that the authentication start processing is detected. The operation procedure may proceed to turn-on processing of the illumination unit 13 of step St2A, or proceed to the processing of step St5 while omitting the processing of step St2A. When the processing of step St2A is omitted and the operation procedure proceeds to the processing of step St5, the biological authentication system 100 turns on the illumination unit 13 in step St2B.

In addition, the biological authentication system 100 may execute not only the above-described stationary detection processing of the hand but also, for example, timeout determination performed in the processing of step St8 similarly to the insertion detection of the hand (that is, the processing of step St3 and step St4). In such a case, a predetermined time limit used for the timeout determination may be set to a time limit different from that of the insertion detection processing of the hand and the stationary detection processing of the hand. Further, the biological authentication system 100 may execute the timeout determination on the processing from the insertion detection of the hand to the stationary detection of the hand (that is, a series of processing of step St3 to step St6).

In addition, the biological authentication system 100 may execute, by using an illumination (not illustrated) such as an LED provided on the housing upper surface 16A, output (notification) of the authentication result performed in the processing of step St14 and step St15. Specifically, the biological information acquisition device P0 may turn on a green LED when the authentication result transmitted from the authentication device P2 is "OK", and may notify (output to) the user of the authentication result by turning on a red LED when the authentication result is "NG". Further, when it is determined that the timeout has occurred as a result of the processing of step St8, the biological authentication system 100 may notify (output) that the timeout has occurred by the above-described turning on of the LED (for example, turning on of the red LED). Further, the biological information acquisition device P0 may change the output (notification) of the authentication result performed in the processing of step St14 and step St15 to not only a color of the LED, but also, for example, turn-on control and turn-off control of the LED (that is, a display method). For example, the biological information acquisition device P0 may turn on the LED when the authentication result transmitted from the authentication device P2 is "OK", and may cause the LED to blink when the authentication result transmitted from the authentication device P2 is "NG".

As described above, after the stationary state of the hand of the user is detected based on the detection hand image of the user captured by the stationary detection camera 14, the biological information acquisition camera 15 captures the authentication hand image of the user, and therefore, the biological authentication system 100 according to the first embodiment can more stably acquire the authentication hand image used for the biological authentication even when the hand of the user is not in contact with the housing 16. In addition, in the biological authentication system 100, since hands of an unspecified large number of users do not touch the housing 16 or the glass surface 17, it is possible to reduce an opportunity of contact via an unspecified large number of persons and objects from a hygiene viewpoint such as a virus infection countermeasure.

Figure 6:
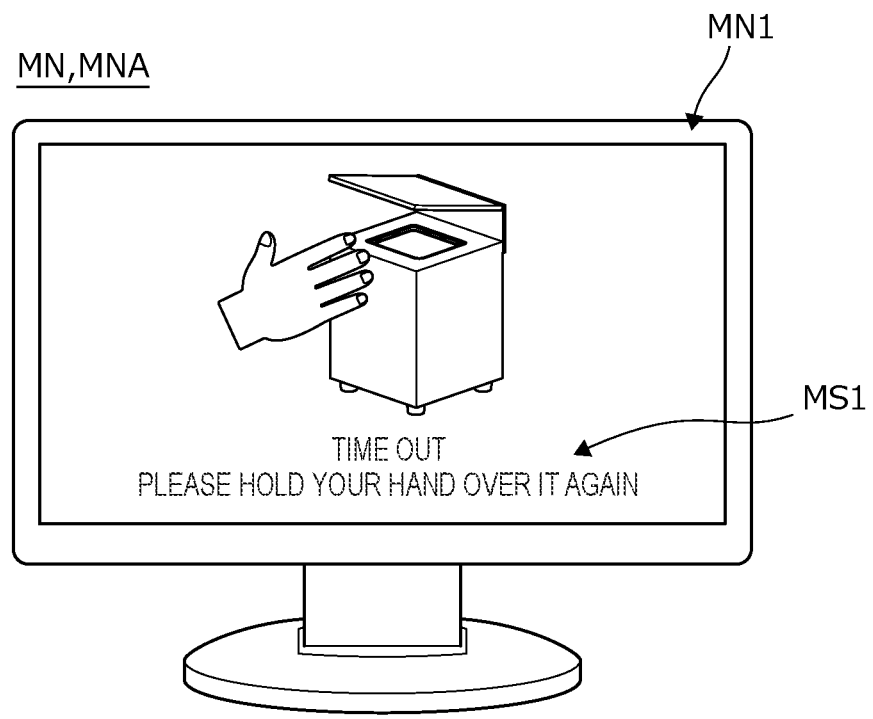
FIG. 6 is a diagram illustrating an example of a timeout notification screen.

The timeout notification screen MN1 will be described with reference to FIG. 6. FIG. 6 is a diagram illustrating an example of the timeout notification screen MN1.

When the stationary state of the hand of the user is not detected within the predetermined time limit based on the detection hand image captured by the stationary detection camera 14, the biological information acquisition device P0 generates the timeout notification screen MN1, outputs the timeout notification screen MN1 to the monitor MN, and causes the monitor MN to display the timeout notification screen MN1. The timeout notification screen MN1 is generated and includes a message MS1 "time out, please hold your hand over it again" for notifying that a timeout has occurred. A content of the message MS1 is not limited to the example illustrated in FIG. 6.

Figure 7:
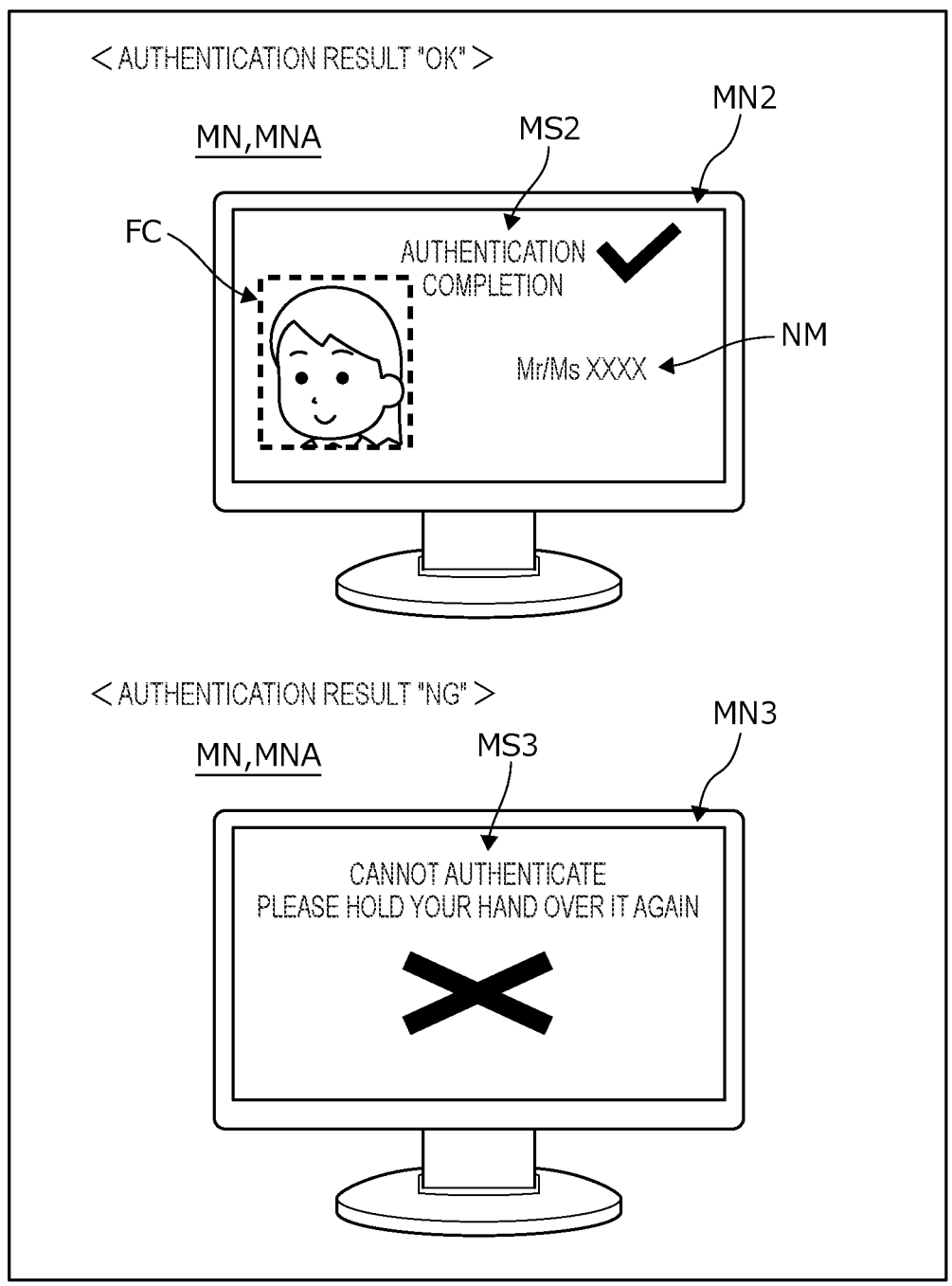
FIG. 7 is a diagram illustrating an example of an authentication result notification screen.

The authentication result notification screens MN2 and MN3 will be described with reference to FIG. 7. FIG. 7 is a diagram illustrating examples of the authentication result notification screens MN2 and MN3. The authentication result notification screen MN2 illustrated in FIG. 7 is an example, and may be a screen including only one of a message MS2, a face image FC, and user information NM.

When the authentication result of the user authentication processing based on the finger image or the biological information of the user transmitted from the biological information acquisition device P0 is "OK" (that is, the biological information of the user transmitted from the biological information acquisition device P0 is present in the biological information of the plurality of users stored (registered) in the biological information database DB), the authentication device P2 generates the authentication result notification screen MN2 notifying that the authentication result is "OK". The authentication result notification screen MN2 is generated and includes, for example, the message MS2, the face image FC, and the user information NM.

The message MS2 includes a message "authentication completion" indicating that the authentication result is "OK". The message MS2 illustrated in FIG. 7 is an example, and is not limited thereto. The face image FC is a face image of a user stored (registered) in the biological information database DB in association with the biological information of the user. The user information NM is information related to the user and is information such as a name and an identification number of the user. The user information NM illustrated in FIG. 7 indicates the name of the user as an example, and "Mr/Ms. xxxx" is displayed.

When the authentication result of the user authentication processing based on the finger image or the biological information of the user transmitted from the biological information acquisition device P0 is "NG" (that is, the biological information of the user transmitted from the biological information acquisition device P0 is not present in the biological information of the plurality of users stored (registered) in the biological information database DB), the authentication device P2 generates the authentication result notification screen MN3 notifying that the authentication result is "NG". The authentication result notification screen MN3 is generated and includes, for example, a message MS3.

The message MS3 is, for example, a message indicating that the authentication result is "NG", such as "cannot authenticate, please hold your hand over it again". The message MS3 illustrated in FIG. 7 is an example, and is not limited thereto.

Second Embodiment

The biological authentication system 100 according to the first embodiment described above illustrates an example in which the biological information acquisition device P0 and the authentication device P2 are connected to be able to transmit and receive data via the network NW. In a biological authentication system 100A according to a second embodiment, an example in which a biological information acquisition device P0A and an authentication device P2A are connected to be able to transmit and receive data without the intervention of the network NW will be described.

Figure 8:
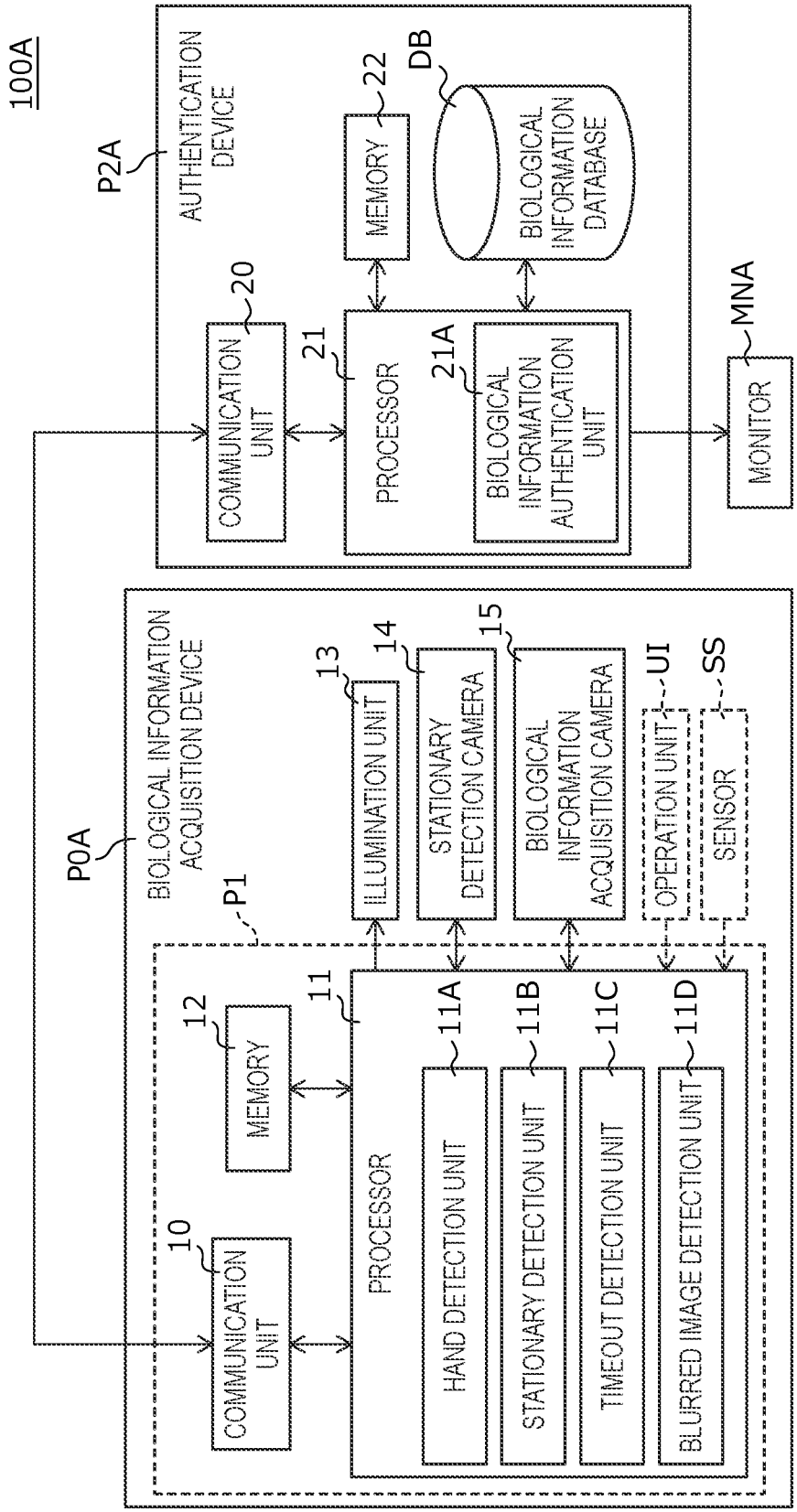
FIG. 8 is a diagram illustrating an internal configuration example of a biological information acquisition device and an authentication device according to a second embodiment.

First, the biological authentication system 10A, the biological information acquisition device P0A, and the authentication device P2A according to the second embodiment will be described with reference to FIG. 8. FIG. 8 is a diagram illustrating an internal configuration example of the biological information acquisition device P0 and the authentication device P2 according to the second embodiment. The same components as those of the biological authentication system 100, the biological information acquisition device P0, and the authentication device P2 according to the first embodiment are denoted by the same reference numerals, and the description thereof is omitted.

The biological information acquisition device P0A and the authentication device P2A according to the second embodiment are connected to be able to transmit and receive data to and from each other. In addition, a monitor MNA according to the second embodiment is connected to the authentication device P2A and displays the timeout notification screen MN1 or the authentication result notification screens MN2 and MN3 output from the authentication device P2A.

Figure 9:
FIG. 9 is a table illustrating a correspondence relationship between an operation procedure example illustrated in FIG.

Here, a correspondence relationship between the operation procedure example of the biological authentication system 100 according to the first embodiment illustrated in FIG. 5 and an operation procedure example of the biological authentication system 100A according to the second embodiment will be described with reference to FIG. 9. FIG. 9 is a table TB illustrating a correspondence relationship between the operation procedure example illustrated in FIG. 5 and the operation procedure example of the biological authentication system according to each embodiment. A relationship between the operation procedure example of the biological authentication system 100 according to the first embodiment illustrated in FIG. 5 and a biological authentication device 100B according to a third embodiment will be described in detail in the third embodiment.

In the biological authentication system 100A according to the second embodiment, in the operation procedure example of the biological authentication system 100 according to the first illustrated in FIG. 5, the processing of step St1 to step St11, step St14, and step St15 is executed by the biological information acquisition device P0A, and the processing of step St12 and step St13 is executed by the authentication device P2A.

Third Embodiment

The biological authentication system 100 according to the first embodiment described above illustrates an example in which the biological information acquisition device P0 and the authentication device P2 are separately configured. In the biological authentication device 100B according to the third embodiment, an example in which a biological information acquisition device P0B and an authentication device P2B are integrally configured will be described.

First, the biological authentication device 100B, the biological information acquisition device P0B, and the authentication device P2B according to the third embodiment will be described with reference to FIG. 10. FIG. 10 is a diagram illustrating an internal configuration example of the biological information acquisition device P0B and the authentication device P2B according to the third embodiment. The same configurations as those of the biological information acquisition device P0 and the authentication device P2 according to the first embodiment or the biological information acquisition device P0A and the authentication device P2A according to the second embodiment are denoted by the same reference numerals, and the description thereof is omitted.

The biological authentication device 100B according to the third embodiment includes the biological information acquisition device P0B and the authentication device P2B which are integrally configured. In addition, the biological information acquisition device P0B includes the illumination unit 13, the stationary detection camera 14, and the biological information acquisition camera 15. The operation unit UI and the sensor SS are not necessary components and may be omitted.

The illumination unit 13 is controlled to be turned on or off by a processor 21B. The stationary detection camera 14 captures an image of the hand of the user under the control of the processor 21B, and outputs the captured detection hand image of the user to the processor 21B in the authentication device P2B. The biological information acquisition camera 15 captures an image of the hand of the user under the control of the processor 21B, and outputs the captured authentication hand image of the user to the processor 21B.

Similarly, the operation unit UI receives an operation of the administrator, and outputs the received operation of the administrator to the processor 21B. When the hand of the user is detected in a predetermined detection region, the sensor SS outputs the detection result to the processor 21B.

The authentication device P2B according to the third embodiment includes the processor 21B, a memory 22B, and the biological information database DB. In addition, similarly to the authentication device P2A according to the second embodiment, the authentication device P2B according to the third embodiment is communicably connected to the monitor MN, outputs the timeout notification screen MN1 or the authentication result notification screens MN2 and MN3 to the monitor MN, and causes the monitor MN to display the timeout notification screen MN1 or the authentication result notification screens MN2 and MN3.

The processor 21B is implemented with, for example, a CPU or an FPGA, and performs various types of processing and control in cooperation with the memory 22B. Specifically, the processor 21B refers to a program and data stored in the memory 22B, and executes the program to acquire the authentication hand image of the user or the biological information of the user, and implements the functions of the units for executing the user authentication. The units referred to here are the biological information authentication unit 21A, a hand detection unit 23A, a stationary detection unit 23B, a timeout detection unit 23C, and a blurred image detection unit 23D.

In the units of the processor 21B according to the third embodiment, the hand detection unit 23A corresponds to the hand detection unit 11A according to the first embodiment and implements the same function, the stationary detection unit 23B corresponds to the stationary detection unit 11B according to the first embodiment and implements the same function, the timeout detection unit 23C corresponds to the timeout detection unit 11C according to the first embodiment and implements the same function, the blurred image detection unit 23D corresponds to the blurred image detection unit 11D according to the first embodiment and implements the same function, and thus detailed description thereof will be omitted.

Here, a correspondence relationship between the operation procedure example of the biological authentication system 100 according to the first embodiment illustrated in FIG. 5 and an operation procedure example of the biological authentication device 10B according to the third embodiment will be described with reference to FIG. 9 again.

In the biological authentication device 100B according to the third embodiment, in the operation procedure example of the biological authentication system 100 according to the first embodiment illustrated in FIG. 5, the processing of step St1 to step St3, step St5, step St7, and step St11 is executed by the biological information acquisition device P0B, and the processing of step St4, step St6, step St8 to step St10, and step St12 to step St15 is executed by the authentication device P2B.

As described above, the biological authentication device 100B according to the third embodiment can acquire the authentication hand image as the biological information of the user and execute the user authentication by one device. In addition, since the biological authentication device 100B according to the third embodiment does not transmit and receive data such as a finger image, biological information, or a face image of the user via the network NW, it is possible to prevent leakage of personal information to outside.

As described above, each of the biological information acquisition devices P0 and P0A according to the first and second embodiments includes the stationary detection camera 14 (an example of the first camera) that images the detection hand image (an example of a first hand image) of the user inserted into the imaging region, the biological information acquisition camera 15 (an example of the second camera) that captures the authentication hand image (an example of a second hand image) of the user used for the biological authentication, and the processor 11 that causes the biological information acquisition camera 15 to capture the authentication hand image when the stationary state of the hand is detected based on the detection hand image captured by the stationary detection camera 14.

As described above, each of the biological authentication systems 100 and 100A according to the first and second embodiments captures the authentication hand image of the user by the biological information acquisition camera 15 after the stationary state of the hand of the user is detected based on the detection hand image of the user captured by the stationary detection camera 14, and therefore, the biological authentication systems 100 and 100A can more stably capture an authentication finger image used for the biological authentication even when the hand of the user is not in contact with the housing 16. In addition, in each of the biological authentication systems 100 and 100A, since hands of an unspecified large number of users do not touch the housing 16 or the glass surface 17, it is possible to reduce an opportunity of contact via an unspecified large number of persons and objects from a hygiene viewpoint such as a virus infection countermeasure.

In addition, as described above, when the processor 11 determines that the hand of the user is inserted into the imaging region based on the detection hand image captured by the stationary detection camera 14, the processor 11 determines whether the hand is stationary. Accordingly, each of the biological authentication systems 100 and 100A according to the first and second embodiments can detect whether the hand of the user is sufficiently inserted into the imaging region in the capture of the authentication hand image for the biological authentication.

In addition, as described above, the processor 11 determines whether the hand is stationary based on a pixel difference between a latest detection hand image captured by the stationary detection camera 14 and a past detection hand image captured before the latest detection hand image. Accordingly, since each of the biological authentication systems 100 and 100A according to the first and second embodiments can detect whether the hand of the user is stationary, the biological authentication systems 100 and 100A can more stably capture the authentication hand image used for the biological authentication even when the hand of the user is in a non-contact state.

In addition, as described above, the processor 11 determines whether the hand is inserted based on a pixel difference between the latest detection hand image captured by the stationary detection camera 14 and a background image of the imaging region captured in advance. Accordingly, each of the biological authentication systems 100 and 100A according to the first and second embodiments can detect whether the hand of the user is sufficiently inserted into the imaging region in the capture of the authentication hand image for the biological authentication.

In addition, as described above, the processor 11 detects the hand shown in the detection hand image captured by the stationary detection camera 14, and determines that the hand is inserted into the imaging region when a part of the detected hand is positioned above the detection line L set on the angle of view of the detection hand image. Accordingly, each of the biological authentication systems 100 and 100A according to the first and second embodiments can detect whether the hand of the user is sufficiently inserted into the imaging region in the capture of the authentication hand image for the biological authentication.

As described above, each of the biological information acquisition devices P0 and P0A according to the first and second embodiments further includes the illumination unit 13 that illuminates the hand inserted in the imaging region. The processor 11 turns on the illumination unit 13 when the stationary state of the hand is detected. Accordingly, since each of the biological authentication systems 100 and 100A according to the first and second embodiments illuminates the hand of the user in the capture of the authentication hand image for the biological authentication, the biological authentication systems 100 and 100A can more clearly capture the authentication hand image used for the biological authentication even when the hand of the user is in a non-contact state.

In addition, as described above, the processor 11 turns on the illumination unit 13 when the insertion of the hand is detected. Accordingly, since each of the biological authentication systems 100 and 100A according to the first and second embodiments illuminates the hand of the user in the capture of the detection hand image used for the stationary detection of the hand, the biological authentication systems 100 and 100A can more clearly capture the detection hand image used for the stationary detection of the hand.

In addition, as described above, each of the biological information acquisition devices P0 and P0A according to the first and second embodiments further includes the operation unit UI that receives an external operation. The processor 11 turns on the illumination unit 13 based on, for example, an external operation by an administrator or the like. Accordingly, each of the biological authentication systems 100 and 100A according to the first and second embodiments can more clearly capture the detection hand image and the authentication hand image by illuminating the hand of the user in the capture of the detection hand image and the authentication hand image of the user.

In addition, as described above, the frame rate of the stationary detection camera 14 is greater than the frame rate of the biological information acquisition camera 15. Accordingly, each of the biological authentication systems 100 and 100A according to the first and second embodiments can execute capture of the detection hand image suitable for the stationary detection and capture of the authentication hand image suitable for the biological authentication.

In addition, as described above, the resolution of the stationary detection camera 14 is smaller than the resolution of the biological information acquisition camera 15. Accordingly, each of the biological authentication systems 100 and 100A according to the first and second embodiments can execute capture of the detection hand image suitable for the stationary detection and capture of the authentication hand image suitable for the biological authentication.

As described above, the biological authentication device MOB according to the third embodiment includes the stationary detection camera 14 that images the hand of the user inserted into the imaging region, the biological information acquisition camera 15 that images the hand of the user, and the processor 21B (an example of an output unit) that causes the biological information acquisition camera 15 to image the hand when the stationary state of the hand is detected based on the detection hand image of the user captured by the stationary detection camera 14, acquires the biological information of the user based on the hand image of the user captured by the biological information acquisition camera 15, and outputs a collation result obtained by collating the acquired biological information with the biological information of the plurality of users registered in advance. Accordingly, the biological authentication device 100B according to the third embodiment can more stably capture the authentication hand image used for the biological authentication even when the hand of the user is not in contact with the housing 16, and can execute the user authentication based on the biological information of the user extracted from the captured authentication hand image. In addition, in the biological authentication device 100B according to the third embodiment, since hands of an unspecified large number of users do not touch the housing 16 or the glass surface 17, it is possible to reduce an opportunity of contact via an unspecified large number of persons and objects from a hygiene viewpoint such as a virus infection countermeasure.

Although various embodiments have been described above with reference to the accompanying drawings, the present disclosure is not limited thereto. It is apparent to those skilled in the art that various modifications, corrections, substitutions, additions, deletions, and equivalents can be conceived within the scope described in the claims, and it is understood that such modifications, corrections, substitutions, additions, deletions, and equivalents also fall within the technical scope of the present disclosure. In addition, components in the various embodiments described above may be freely combined without departing from the gist of the invention.

The present application is based on Japanese Patent Application No. 2020-182605 filed on Oct. 30, 2020, the contents of which are incorporated herein by reference.

INDUSTRIAL APPLICABILITY

The present disclosure is useful as presentation of a biological information acquisition device, a biological authentication device, and a biological information acquisition method capable of stably acquiring a hand image used for biological authentication even in a non-contact state.

REFERENCE SIGNS LIST

10, 20: communication unit
11, 21, 21B: processor
11A, 23A: hand detection unit
11B, 23B: stationary detection unit
11C, 23C: timeout detection unit
11D, 23D: blurred image detection unit
12, 22, 22B: memory
13: illumination unit
14: stationary detection camera
15: biological information acquisition camera
21A: biological information authentication unit
100, 100A: biological authentication system
100B: biological authentication device
DB: biological information database
L: detection line
MN, MNA: monitor
NW: network
P0, P0A, P0B, P3: biological information acquisition device
P1: control device
P2, P2A, P2B: authentication device
UI: operation unit

The invention claimed is:

1. A biological information acquisition device, comprising:
a first camera configured to capture at least one first hand image of a user based on a hand of the user being inserted into an imaging region;
a second camera configured to capture a second hand image of the user, the second hand image being used for biological authentication; and
a processor configured to cause the second camera to capture the second hand image when a stationary state of the hand of the user is detected based on the at least one first hand image captured by the first camera,
wherein, when the processor determines, based on the at least one first hand image captured by the first camera, that the hand of the user is inserted into the imaging region, the processor determines whether the hand is stationary, and the processor is further configured to determine whether the hand is inserted into the imaging region based on a pixel difference between a latest first hand image captured by the first camera and a background image of the imaging region captured in advance.

2. The biological information acquisition device according to claim 1, wherein
the processor is configured to determine whether the hand is stationary based on a pixel difference between the latest first hand image captured by the first camera and a past first hand image captured before the latest first hand image.

3. The biological information acquisition device according to claim 1, wherein
the processor is configured to detect the hand shown in the at least one first hand image captured by the first camera, and determine that the hand is inserted into the imaging region when a part of the hand is positioned on a detection line set on an angle of view of the 1t least one first hand image.

4. The biological information acquisition device according to claim 1, further comprising:
a light configured to illuminate the hand inserted into the imaging region, wherein
the processor is configured to turn on the light when the stationary state of the hand is detected.

5. The biological information acquisition device according to claim 4, wherein
the processor is configured to turn on the light when insertion of the hand is detected.

6. The biological information acquisition device according to claim 4, further comprising:
a user interface configured to receive an external operation, wherein
the processor is configured to turn on the light based on the external operation.

7. The biological information acquisition device according to claim 1, wherein
a frame rate of the first camera is higher than a frame rate of the second camera.

8. The biological information acquisition device according to claim 1, wherein
a resolution of the first camera is lower than a resolution of the second camera.

9. A biological authentication device, comprising:
a first camera configured to image a hand of a user, the hand of the user being inserted into an imaging region;
a second camera configured to image the hand of the user; and
a processor configured to cause the second camera to image the hand when a stationary state of the hand is detected based on at least one first hand image of the hand of the user captured by the first camera,
wherein the processor is further configured to acquire biological information of the user based on a second hand image of the user captured by the second camera, and output a collation result obtained by collating the acquired biological information with biological information of a plurality of users registered in advance,
when the processor determines, based on the at least one first hand image captured by the first camera, that the hand of the user is inserted into the imaging region, the processor determines whether the hand is stationary, and
the processor determines whether the hand is inserted into the imaging region based on a pixel difference between a latest first hand image captured by the first camera and a background image of the imaging region captured in advance.

10. A biological information acquisition method of a biological information acquisition device, the biological information acquisition device imaging a hand of a user using a first camera and a second camera, the biological information acquisition method comprising:
imaging, by the first camera, the hand of the user, the hand of the user being inserted into an imaging region; and
imaging the hand of the user by a second camera when a stationary state of the hand is detected based on at least one captured hand image of the hand of the user,
wherein, when the biological information acquisition device determines, based on the at least one captured hand image of the hand of the user, that the hand of the user is inserted into the imaging region, the biological information acquisition device determines whether the hand is stationary, and
the biological information acquisition device determines whether the hand is inserted into the imaging region based on a pixel difference between a latest first hand image captured by the first camera and a background image of the imaging region captured in advance.

* * * * *